United States Patent

Miyata et al.

[11] Patent Number: 4,770,129
[45] Date of Patent: Sep. 13, 1988

[54] SENSOR FOR MIXING RATIO OF GASOLINE AND ALCOHOL

[75] Inventors: Shigeru Miyata; Yoshihiro Matsubara, both of Nagoya, Japan

[73] Assignee: NGK Spark Plug Co., Ltd., Nagoya, Japan

[21] Appl. No.: 45,072

[22] Filed: May 1, 1987

[51] Int. Cl.$^4$ ............................................. F02B 75/00
[52] U.S. Cl. ..................................... 123/1 A; 423/494
[58] Field of Search ................................. 123/1 A, 494

[56] References Cited

U.S. PATENT DOCUMENTS 4,541,272  9/1985  Bause ................................... 123/494
4,594,968  6/1986  Degobert et al. ................... 123/1 A Primary Examiner—E. Rollins Cross
Attorney, Agent, or Firm—Cooper & Dunham

[57] ABSTRACT

A sensor for mixing ratio of gasoline and alcohol comprising: a transparent column, both ends of which are supported by grips; the surface of the column is positioned in direct contact with a mixing liquid of gasoline and alcohol; a light emitting diode disposed so that light beams therefrom are incident on one end of said transparent column and the mixing liquid, said beams incident on said boundary at less than a critical angle being totally refracted, while said beams incident on said boundary at more than the critical angle being totally reflected to pass within said column so as to go out from the other end thereof, said critical angle depending upon a mixing degree of said liquid; a photo diode placed to receive the light beams reflected from the boundary so as to generate an output in accordance with the quantity of the light beams received; and the column being substantially determined its lengthwise and diametrical dimension such that the light beams incident upon the boundary at a critical angle, are allowed to totally reflect only once to enter the photo diode with the mixing ratio of alcohol and gasoline ranging from 100:0 to 0:100.

2 Claims, 3 Drawing Sheets

SENSOR FOR MIXING RATIO OF GASOLINE AND ALCOHOL

BACKGROUND OF THE INVENTION

1. Field of the Invention

This invention relates to a sensor which detects mixing ratio of gasoline and alcohol employed to as a fuel of internal combustion engine for example.

2. Description of the Prior Art

Of these days, it is planned to extract liquid alcohol from plants. The alcohol thus extracted is mixed with gasoline to use as liquid fuel for internal combustion engine. When employed to an internal combustion engine for motor vehicle, it is necessary to precisely control the mixing ratio of the liquid fuel to obtain maximum output level and avoid adverse effect upon human health due to harmful exhaust gas. This precise control is naturally executed each time when the kind of the liquid fuel changes. When the mixing liquid of gasoline and alcohol is put into market, it is preferable that the mixing liquid is used together with the gasoline.

Therefore, it is an object of this invention to provide an improved sensor which is capable of continuously measuring a ratio of alcohol and gasoline with high precision in order to obtain most appropriate timing of ignition and injection when employed to an internal combustion engine.

According to the invention, a transparent column, both ends of which are supported by grips; the surface of said column is positioned in direct contact with a mixing liquid of gasoline and alcohol; a light emitting diode disposed so that light beams therefrom are incident on one end of said transparent column and the mixing liquid, said beams incident on said boundary at less than a critical angle being totally refracted, while said beams incident on said boundary at more than the critical angle being totally reflected to pass within said column so as to go out from the other end thereof, said critical angle depending upon a mixing degree of said liquid; a photo diode placed to receive the light beams reflected from said boundary so as to generate an output in accordance with the quantity of the light beams received; and said column being substantially determined its lengthwise and diametrical dimension such that the light beams incident upon said boundary at a critical angle, are allowed to totally reflect only once to enter said photo diode with the mixing ratio of alcohol and gasoline ranging from 100:0 to 0:100.

DESCRIPTION OF THE PREFERRED EMBODIMENTS

Figure 1:
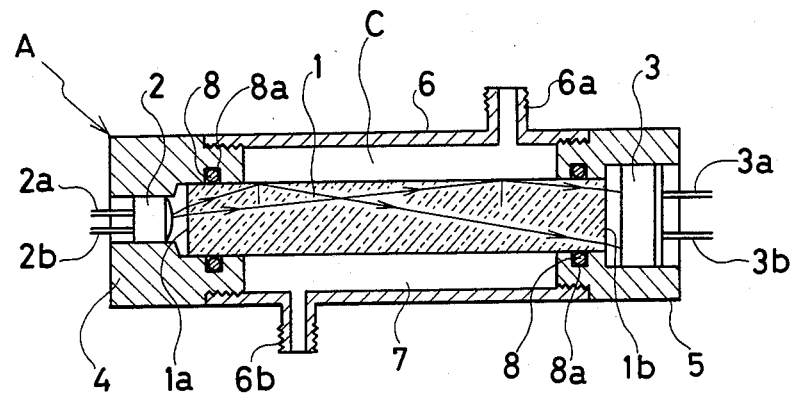
FIG. 1 is a longitudinal cross-section view of a sensor.

Referring to the drawings, an embodiment of the invention is described.

Firstly, attention is called to FIG. 1 of the drawings in which longitudinal sectional view of a sensor device is shown. A transparent column 1 which is made of glass, is interfit at each end into a cylindrical grips 4, 5 each of which is made from metal or synthetic resin. Into the grip 4, a light emitting diode 2 is concentrically placed to face the emitting portion against one end 1a of the column 1.

Numerals 2a, 2b designate input terminals of the diode 2. Into the grip 5, a photo diode 3 is concentrically placed to face the light beams receiving portion against the other end of the column 1. Numerals 3a, 3b designate output terminals of the photo diode 3. Between the grips 4 and 5, a cylindrical casing 6 is interfit to connect therebetween. An annular space is established between the inner surface of the casing 6 and the outer surface of the column 1 to serve as a reservoir 7 to make a mixture liquid in contract with the outer surface of the column 1 at the time of measuring ratio of the liquid mixture. Inlet and outlet couples 6a, 6b are mounted on the casing 6 to be in communication with the inner side of the reservoir 7. Each of the grips 4, 5 has a groove 8a at the inner wall into which a O-ring 8 is interfit to prevent the liquid mixture from leaking between the inner wall and the outer surface of the column 1.

Figure 3:
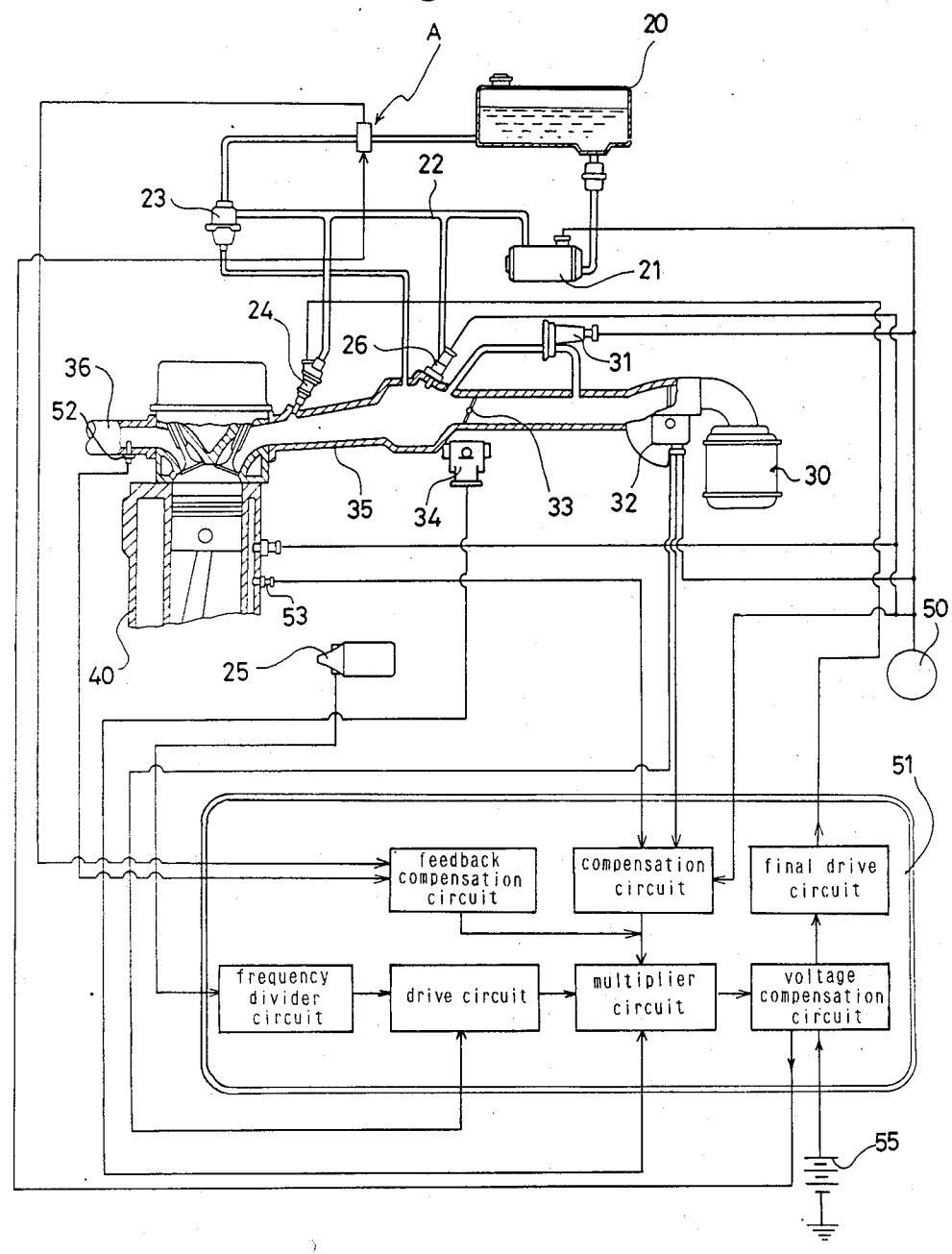
FIG. 3 is a schematic diagram of an electronic fuel injection control device for automobile engine.

FIG. 3 shows a schematic diagram of control system for automobile engine into which electronic control fuel injection is associated. In FIG. 3, numeral 40 shows an engine cylinder, numeral 50 a key switch of the engine, numeral 51 control circuit, numeral 55 an electrical source mounted on the automobile, numeral 20 fuel tank, denotation A designates a sensor which detects a mixture ratio of gasoline and alcohol. Numeral 21 is a fuel pump referred to as a primary constituent of fuel system, numeral 23 a pressure regulator, numeral 24 an injector, numeral 26 a cold start injector, numeral 25 an ignition coil, numeral 30 an air cleaner, numeral 31 an air valve, numeral 32 an air flow meter, numeral 33 a throttle valve, numeral 34 a throttle position sensor, numeral 35 an intake pipe, numeral 36 an exhaust pipe. Numerals 52 and 53 designate an oxygen sensor and a water temperature sensor respectively.

In operation, the key switch 50 is set at the start position to start the engine, and power is supplied to the control circuit 51. On the other hand, the liquid mixture which is the mixture of gasoline and alcohol at the appropriate ratio to serve as a fuel contained in the fuel tank 20, is introduced into the injector 24 by the pump 21 through a fuel pipe 22. The injector 24 injects the best suited amount of the liquid mixture into the intake pipe 35 in accordance with the control circuit 51.

Meanwhile, the sensor A is connected to the intermediate of the pipe 22 through the couples 6a, 6b. The power is applied to the diode 2 from the control circuit 51 to emit light beams which falls on one end 1a of the column 1. The light beams incident on the boundary between the liquid mixture and the column 1, totally reflects and pass through the column 1 to fall on the photo diode 3, if the indicent angle is greater than the critical angle. The photo diode 3 thus subjected to the light beams, is activated to produce an output proportional to the amount of the light beams across the terminals 3a, 3b.

On the other hand, the light beams incident upon the boundary the incident angle of which is smaller than the critical angle, refracts at the boundary to escape out of the column 1, and substantially has no affect upon the output of the diode 3. The critical angle at the boundary of the liquid mixture (C), changes depending upon the mixing ratio of gasoline and alcohol (generally referred to as methyl alcohol), so the light beam which emits from the diode 2 and reflects at the boundary only once to be caught by the diode 3, changes in its magnitude according to the mixing ratio of gasoline and alcohol.

Consequently, it is obviously possible to reduce the output of the photo diode 3 into the mixing ratio of gasoline and alcohol by the use of an electronic circuit when the relation between the output of the diode and the mixing ratio of gasoline and alcohol is previously obtained through a series of experimentations.

Figure 4:
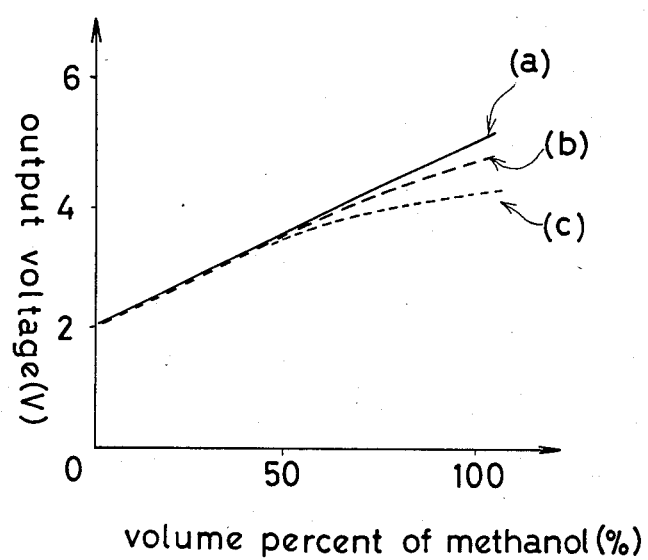
FIG. 4 is a graph showing a relationship between the output of a sensor and a mixing ratio of gasoline and alcohol.

Meanwhile, the inventors tried a series of experimentations how the relationship between the output of the photo diode 3 and the mixing ratio of gasoline and alcohol changes depending upon the alteration of dimension and mounting of the column 1. As is seen in FIG. 4, the change of axial length with dimension shows generally liner within the relatively short range with the diametrical dimension being constant. With the further extensive range, the graph of FIG. 4 is found to get out of linearity.

In FIG. 4, the case (a) shows that a relatively long column is employed, while the case (b) shows a column longer than the case (a) is employed. The case (c) shows a column further longer than the case (b) is employed.

It is apparent that as the relationship between the output of the photo diode 3 and the mixing ratio of gasoline and alcohol, approaches to linearity, more precise measurement result is obtained. Therefore, it is desirable to provide a sensor having a characteristic as shown at (a) of FIG. 4. The linear degree in FIG. 4 progressively decreases as shown from (b) to (c) due in main to the fact that as the column 1 increases the lengthwise dimension, the light beams gets increased times of reflection and requires extended light beams path so as to increase optical loss.

The result obtained above teaches as follows:

In order to provide a sensor device which is capable of obtaining high precision measurement by maintaining linear relationship between the output of the photo diode 3 and the optical requirement is that the column 1 is substantially determined its lengthwise and diametrical dimension such that the light beams incident upon the boundary at a critical angle, are allowed to totally reflect only once to enter the photo diode 3 with the mixing ratio of alcohol and gasoline ranging from 100:0 to 0:100.

By way of illustration, dimension of the part component of the sensor A is determined as follows:

L: lengthwise dimension of the column 1 r: radius of the column 1 d: overlapping length of the grip 4 and end portion 1a of the column d': overlapping length of the grip 5 and end portion 1b of the column D: lengthwise dimension of L minus d' n: distance between emitting surface of the diode 2 and end portion 1a of the column 1

Figure 2:
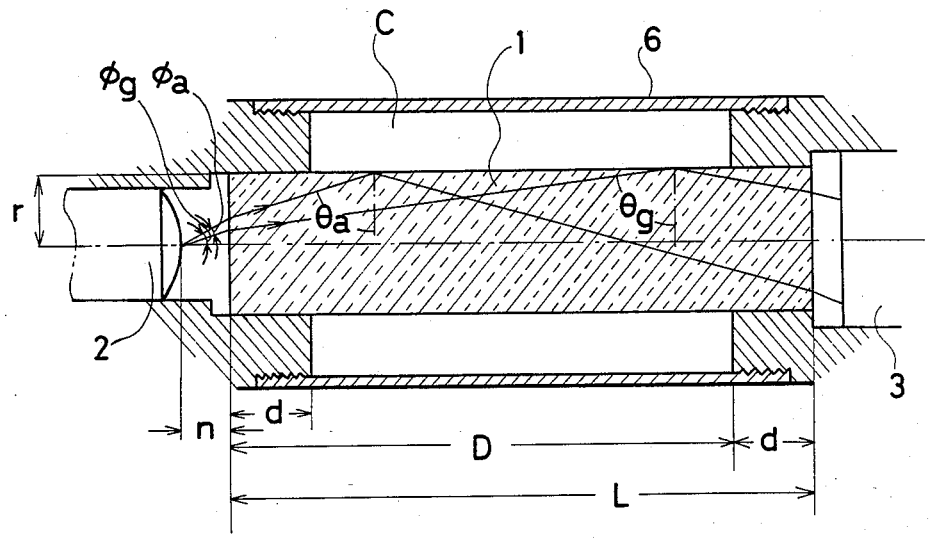
FIG. 2 is a schematic view of light path to determine the lengthwise and diametrical dimensions of a column.

$\theta a$: critical angle of the column 1 against 100% alcohol $\phi a$: incident to form the critical angle $\theta a$ $\theta g$: critical angle of the column 1 against 100% gasoline $\phi g$: incident angle to form the critical angle $\theta g$ The following equations (1)~(3) are obtained so as to satisfy the optical requirement in reference to geometrical relationship of FIG. 2.

$$L < (3r - n \tan \phi a) \tan \theta a \quad (1)$$

$$D > (r - n \tan \phi g) \tan \theta g \quad (2)$$

$$d < (r - n \tan \phi a) \tan \theta a \quad (3)$$

In connection with incident angle $\phi$ and critical angle $\theta$, these angles are measured under the temperature of 20 degrees centigrade as below.

$\phi a = 39.4°$
$\theta a = 64.4°$
$\phi g = 20.9°$
$\theta g = 75.9°$

By substituting these angles into the equations (1) (3), dimensions L<10.6 (mm), D>5.8 (mm) and d<2.1 (mm) are obtained with the dimensions r and n being 2 (mm) and 1.2 (mm) respectively.

What is claimed is:

1. A sensor for mixing ratio of gasoline and alcohol comprising:

a transparent column, both ends of which are supported by grips; the surface of said column is posited in direct contact with a mixing liquid of gasoline and alcohol; a light emitting diode disposed so that light beams therefrom are incident on one end of said transparent column and the mixing liquid, said beams incident on said boundary at less than a critical angle being totally refracted, while said beams incident on said boundary at more than the critical angle being totally reflected to pass within said column so as to go out from the other end thereof, said critical angle depending upon a mixing degree of said liquid; a photo diode placed to receive the light beams reflected from said boundary so as to generate an output in accordance with the quantity of the light beams received; and said column being substantially determined its lengthwise and diametrical dimension such that the light beams incident upon said boundary at a critical angle, are allowed to totally reflect only once to enter said photo diode with the mixing ratio of alcohol and gasoline ranging from 100:0 to 0:100.

2. In a sensor as recited in claim 1, dimensional relationship amount L, D, d, r, $\phi a$, $\theta a$, $\phi g$ and $\theta g$ are determined as follows:

$$L < (3r - n \tan \phi a) \tan \theta a$$

$$D > (r - n \tan \phi g) \tan \theta g$$

$$d < (r - n \tan \phi a) \tan \theta a$$

where

L: lengthwise dimension of said column, r: radius of said column d: insertion depth of said column to the grip at one end d': insertion depth of said column to the grip at the other end D: (L−d')

n: distance between the emitting diode and one end of column $\theta a$: a critical angle formed when a light totally reflects at a boundary between the column and the liquid after entering through one end of the column at an angle of $\phi a$.

$\theta g$: a critical angle formed when a light totally reflects at a boundary between the column and the liquid after entering through one end of the column at an angle of $\phi g$.

* * * * *

UNITED STATES PATENT AND TRADEMARK OFFICE
CERTIFICATE OF CORRECTION

PATENT NO.   :   4,770,129
DATED        :   September 13, 1988
INVENTOR(S)  :   Shigeru Miyata et al It is certified that error appears in the above-identified patent and that said Letters Patent is hereby corrected as shown below:

In sheet 1 of the drawings, Fig. 2 should correctly read:

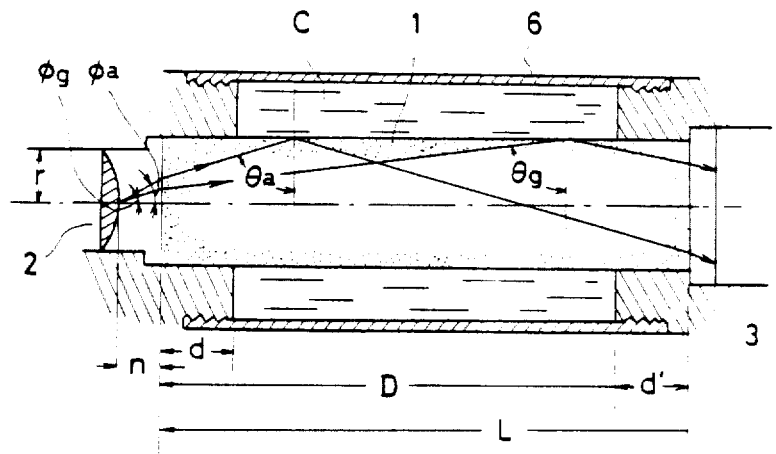

Signed and Sealed this

Eleventh Day of August, 1992

*Attest:*

DOUGLAS B. COMER

*Attesting Officer*          *Acting Commissioner of Patents and Trademarks*